United States Patent [19]
Austin et al.

[11] Patent Number: 5,880,188
[45] Date of Patent: Mar. 9, 1999

[54] OXABOROLES AND SALTS THEREOF, AND THEIR USE AS BIOCIDES

[75] Inventors: Peter William Austin, Bury; Christopher Juan Kneale, Oldham; Patrick Jelf Crowley, Crowthorne; John Martin Clough, Marlow, all of United Kingdom

[73] Assignee: Zeneca Limited, London, England

[21] Appl. No.: 750,081

[22] PCT Filed: May 26, 1995

[86] PCT No.: PCT/GB95/01206

§ 371 Date: Dec. 9, 1996

§ 102(e) Date: Dec. 9, 1996

[87] PCT Pub. No.: WO95/33754

PCT Pub. Date: Dec. 14, 1995

[30] Foreign Application Priority Data

Jun. 9, 1994 [GB] United Kingdom ................ 9411587.0

[51] Int. Cl.$^6$ ............................ C08K 5/15; A01N 55/08; C07F 5/04
[52] U.S. Cl. .......................... 524/109; 524/111; 424/405; 514/64; 558/288; 558/290; 558/291
[58] Field of Search ............................... 424/405; 514/64; 524/109, 111; 558/288, 290, 291

[56] References Cited

U.S. PATENT DOCUMENTS

| 3,104,255 | 9/1963 | Emrick et al. .......................... 558/290 |
|---|---|---|
| 3,361,672 | 1/1968 | Andress, Jr. et al. ................... 558/290 |
| 3,655,775 | 4/1972 | Nauta ....................................... 558/288 |
| 3,686,398 | 8/1972 | Kohn et al. .............................. 424/185 |

FOREIGN PATENT DOCUMENTS 2 195 401  3/1974  France .

OTHER PUBLICATIONS

Dale et al: "Substituted Styrenes VII The Synthesis and Some Reactions of the Vinylbenzeneboronic Acids", The Journal of Organic Chemistry, vol. 27, 1962, pp. 2598–2603, Table 1, compounds 19 and 20.

Cummings et al: "Arylboronic Acids. A Medium–size Ring Containing Boronic Ester Groups", The Journal of Organic Chemistry, vol. 34, 1969, pp. 1669–1674. see the whole document.

Tschampel et al: "Arylboronic Acids VII. Some Reactions of O–Formylbanzeneboronic Acid", The Journal of Organic Chemistry, vol. 29, 1964, pp. 2168–2172. see the whole document.

Grassberger:"Zum Abbau Von 1,2–Dihydro–1–Hydroxy–2–Organosulfonyl–2,3,1–Benzodiazaborinen Und–Thieno83,2–D)(1,2,3)Diazaborinen in Alkalischer Wassriger Losung", Liebigs Annalen Der Chemie, 1985, pp. 683–688, cited in the application * Compound 5 *.

*Primary Examiner*—Kriellion S. Morgan
*Attorney, Agent, or Firm*—Pillsbury Madison & Sutro LLP

[57] ABSTRACT

A method for the protection of a medium by susceptible to microbial attack by the treatment of the medium with an oxaborale or a salt of an oxaborale.

23 Claims, No Drawings

OXABOROLES AND SALTS THEREOF, AND THEIR USE AS BIOCIDES

This application is the national phase of international application PCT/GB95/01206 filed May 26, 1995 which designated the U.S.

The present invention relates to the use of oxaboroles and salts thereof as industrial biocides, especially fungicides, biocidal compositions containing the oxaboroles including their salts and certain oxaboroles.

No single industrial biocide is ideal for all applications and new biocides are constantly being sought with better activity against individual spoilage micro-organisms, wider spectrum of activity, improved compatibility with the medium in which they are used and improved persistence in use. Safety in use is another important consideration.

A small number of compounds containing an oxaborole ring (hereinafter "oxaborole") have already been described in the literature. These are N-(1,3-dihydro-1-hydroxy-2,1-benzoxaborol-6-yl)-succinamic acid (CA 55 23423c); 4-(1,3-dihydro-1-hydroxy-2,1-benzoxaborol-6-ylazo)-2-naphthoic acid (CA 55 23423c); 1,3-dihydro-1-hydroxy-6-nitro-2,1-benzoxaborole (CA 55 23423b); 6-amino-1,3-dihydro-1-hydroxy-2,1-benzoxaborole and its hydrochloride (CA 55 23423c); 1,3-dihydro-1-hydroxy-7-methyl-2,1-benzoxaborole (CA 55 6473f); 1-(benzyloxy)-1,3-dihydro-2,1-benzoxaborole (CA 61 16084f); 1,3-dihydro-1-hydroxy-N,N-dimethyl-2,1-benzoxaborol-6-amine (CA 1(3) 22633f); 4-bromo-1,3-dihydro-1-hydroxy-2,1-benzoxaborole (CA 1(3) 22633f); 1,1'-oxybis[4-bromo-1,3-dihydro-2,1-benzoxaborole (CA 1(3) 22633f); 1-(cyclohexyloxy)-1,3-dihydro-2,1-benzoxaborole (CA 61 16084f); 1-ethoxy-1,3-dihydro-2,1-benzoxaborole (CA 61 16084f); 3,7-dihydro-1,5-dihydroxy-1H, 3H-benzo[1,2-c: 4,5-c']bis[1,2]oxaborole (CA 61 14698a); 1,3-dihydro-1-hydroxy-6-methyl-2,1-benzoxaborole (CA 61 14698b); 5-bromo-1,3-dihydro-1-hydroxy-2,1-benzoxaborole-6-methanol (CA 51 14698b); 1,1'-oxybis[1,3-dihydro-2,1-benzoxaborole](CA 103(3) 22633f); and boronophthalide (CA 116(13) 129587q). French certificate of utility No 73 29370 discloses boronophthalide (1-hydroxy-3H-1,2-benzoxaborole) and this is the only citation known which discloses that an oxaborole is biologically active. It is disclosed as being useful in inhibiting the growth of micro organisms in aviation fuels. However, at least 100 ppm of the boronophthalide is required to protect the fuel.

It has now been found that compounds containing an oxaborole ring are particularly effective against micro-organisms such as bacteria, algae, yeasts and particularly fungi, especially fungi which cause degradation of plastics materials. The level of microbiological activity now found is surprising in the light of the disclosure in the above utility certificate.

According to the present invention there is provided a method for the protection of a medium susceptible to microbial attack by the treatment of the medium with an effective amount of an oxaborole of general formula (1)

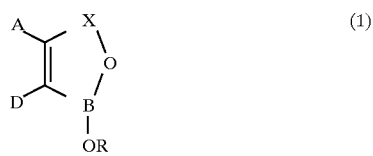

or a salt thereof
wherein

A and D are each independently, hydrogen, optionally substituted $C_{1-8}$-alkyl, aralkyl, aryl, or heterocyclyl or where A and D together with the carbon atoms to which they are attached form a 5,6 or 7-membered fused ring which itself may be substituted;

X is a group —$CR^1R^2$ wherein $R^1$ and $R^2$ are each, independently, hydrogen, optionally substituted $C_{1-6}$-alkyl, nitrile, nitro, aryl or aralkyl or $R^1$ and $R^2$ together with the carbon atom to which they are attached form an alicyclic ring;

R is hydrogen, optionally substituted $C_{1-8}$-alkyl, aralkyl, aryl, heteroaryl, cycloalkyl or a radical of formula (2)

wherein A, D and X are as hereinbefore defined except where the medium is aviation fuel and the only oxaborole is boronophthalide.

When A and/or D is alkyl, it may be linear or branched and is preferably $C_{1-12}$-, more preferably $C_{1-8}$- and especially $C_{1-4}$-alkyl.

When A and/or D is substituted alkyl, the substituent may be $C_{1-6}$-alkoxy, hydroxy, halogen, nitrile, amino, substituted amino, carboxy, acyl, aryloxy or carbonylamnino optionally substituted by $C_{1-6}$-alkyl.

When A and/or D is alkyl the alkyl group or groups are preferably unsubstituted.

When A and/or D is aryl, it is preferably phenyl which may itself be substituted.

When A and/or D is aralkyl, it is preferably benzyl or 2-ethylphenyl, where the phenyl ring may be substituted. when the phenyl ring is substituted, the substituents include $C_{1-6}$-alkyl, $C_{1-6}$-alkoxy, aryloxy, hydroxy, halogen, nitro, carbonamido, sulphonamido, trifluoromethyl or amino optionally substituted by one or more $C_{1-6}$-alkyl groups.

Aryloxy is preferably phenoxy.

When A and D together with the two carbon atoms to which they are attached form a fused ring the ring may be alicyclic as in cyclopentene, cyclohexene or cycloheptene or it may be aromatic such as phenyl, pyridyl, thienyl or furanyl. The fused ring may also carry substituents as described hereinbefore for substituted phenyl and substituted alkyl. The fused ring may also contain more than one ring system, for example, a naphthyl or quinolinyl ring system or the fused ring may also link two oxaborole rings as for example in 1H, 3H-benzo[1,2-c: 4,5-c']bis[1,2] oxaborole.

When $R^1$ and/or $R^2$ is aryl it is preferably phenyl.

When $R^1$ and/or $R^2$ is aralkyl it is preferably benzyl.

Preferably, at least one of $R^1$ and $R^2$ is hydrogen and it is especially preferred that both are hydrogen.

When R is alkyl it may be linear or branched and is preferably $C_{1-12}$- and especially $C_{1-6}$-alkyl.

When R is substituted alkyl, the substitutent may be $C_{1-6}$-alkoxy, $C_{1-6}$-alkylthio, hydroxy, amino, substituted amino, carboxy, aryl, aryloxy, carbonamido optionally substituted by $C_{1-6}$-alkyl, aryl such as phenyl and aralkyl such as benzyl.

When R is aralkyl it is preferably benzyl or 2-ethylphenyl.

When R is aryl it is preferably phenyl.

When R is heteroaryl it is preferably quinolinyl and particularly quinolin-8-yl.

When R is cycloalkyl it is preferably cyclohexyl.

When the substituent is halogen, it is preferably bromine, chlorine and especially fluorine.

One preferred class of oxaborole is a benzoxaborole of formula 1 wherein A and D together with the carbon atoms to which they are attached form a fused phenyl, naphthyl or thienyl ring.

When the fused ring is phenyl, the oxaborole is a benzoxaborole and the substituent or substituents may be in any of positions 4,5,6 or 7 of the benzoxaborole. Preferably the substituent or substituents is/are in the 5 and/or 6 position. Preferred substituents are amino, alkyl, alkoxy, phenyl, phenoxy, sulphonamide, carbonamide, each of which may be substituted, and also trifluoromethyl, chlorine, bromine and especially fluorine.

When the fused ring is naphthyl, the other fused phenyl ring is attached to the benzoxaborole ring system in either the 4,5- or 5,6-position.

In one preferred class of oxaborole, R is hydrogen.

Another preferred class of oxaboroles for use in the present invention is where R is substituted alkyl, especially where the substituent is a primary, secondary or tertiary amino group and particularly wherein the alkylene amino group forms a 5-, 6- or 7-membered ring together with the boron atom and the oxygen atom to which the group R is attached. Such compounds are esters containing a tetrahedral boron atom as for example in formula (3) below

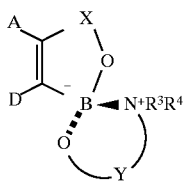

(3)

wherein A,D and X are as defined hereinbefore;

$R^3$ and $R^4$ are each independently, hydrogen, optionally substituted $C_{1-18}$-alkyl or optionally substituted phenyl or $R^3$ together with Y or part of Y forms a 5- or 6- or 7-membered optionally substituted ring containing the nitrogen atom; and Y is an optionally substituted divalent alkylene linking group containing up to 18 carbon atoms.

$R^3$ and $R^4$ are preferably optionally substituted $C_{1-12}$-alkyl, more preferably optionally substituted $C_{1-8}$-alkyl and especially substituted $C_{1-6}$-alkyl.

It is preferred that when $R^3$ and/or $R^4$ is alkyl the alkyl group is unsubstituted.

The alkylene group represented by Y may be linear or branched.

When Y is substituted alkylene the substituent is preferably phenyl, $C_{1-6}$-alkoxy, $C_{1-6}$-alkylthio or carbonyl alkylene as for example a —$COCH_2$— group.

When Y or part of Y forms a 5-, 6- or 7-membered optionally substituted ring the substituent may be a fused ring which may itself be substituted.

Preferably Y is unsubstituted alkylene.

When $R^3$ together with Y forms a 6-membered optionally substituted ring the ring is preferably a quinolinyl ring as obtainable, for example, from 8-hydroxyquinoline.

When $R^3$ together with part of Y forms a 5-membered ring the ring is preferably pyrrolidin-2-yl.

It is preferred that A and D together with the carbon atoms to which they are attached form an aromatic ring or ring system such as for example a fused phenyl, thienyl or naphthyl ring which ring or ring system may be substituted as defined hereinbefore for substituted phenyl and substituted alkyl.

When A and D together with the carbon atoms to which they are attached form a fused phenyl ring which is substituted, the oxaborole may be a 1H, 3H-benzo [1,2-c:4, 5-c'] bis [1,2] oxaborole containing an ester group attached to each boron atom.

A particularly preferred class of oxaborole of formula 3 is that of formula 4

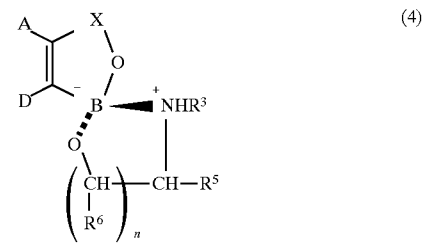

wherein A, D and X are as defined hereinbefore;

n is 1, 2 or 3;

$R^3$ is hydrogen, optionally substituted $C_{1-18}$-alkyl or optionally substituted phenyl;

$R^5$ and $R^6$ are each independently, hydrogen, optionally substituted alkyl containing up to a total of 16 carbon atoms or optionally substituted phenyl.

Preferably $R^5$ and $R^6$ are each, independently, optionally substituted $C_{1-6}$- and especially optionally substituted $C_{1-4}$-alkyl.

Preferably two of $R^3$, $R^5$ and $R^6$ are hydrogen. It is especially preferred that $R^5$ and $R^6$ are both hydrogen.

Preferably n is 1 or 2 and especially 1.

When A and/or D and/or R is a group which is or contains halogen the halogen may be fluorine, chlorine, bromine or iodine. When A and/or D is alkyl substituted by halogen, it may contain more than one halogen atom as in trifluoromethyl.

When A and D together with the two carbon atoms to which they. are attached form a fused ring, any substituent in the fused ring is preferably attached to a carbon atom other than that adjacent to the oxaborole ring. Thus in the case of 1,2-dihydro-2,1-benzoxaboroles the substituent or substituents are preferably in the 5 and/or 6 position.

When the oxaborole of formula 1 is a salt, the group —OR attached to the boron atom is ionic as in —O⁻R⁺ where R⁺ is an alkali metal such as lithium, potassium or sodium or R⁺ is an amine salt or quaternary ammonium cation. In the latter case the quaternary ammonium ion may itself be microbiologically active.

When A and/or D is amino or substituted amino, or when A and/or D and/or R contains amino or substituted amino the salt of the oxaborole of formula I may be the salt of an organic or inorganic acid. Examples of such acids are acetic and hydrochloric acids.

Particularly useful effects have been obtained in plastics materials and paint films where the compound containing an oxaborole ring is benzoxaborole or the 6-chloro-, 5-chloro-, 5-fluoro- or 5-bromo-derivative thereof and the oxaborole esters obtainable therefrom by reaction with alkanoamines such as ethanolamine, 3-aminopropanol and 4-aminobutanol.

The oxaborole may be used in undiluted form but is preferably formulated in a composition together with a carrier. Thus, as a further aspect of the invention there is provided a composition comprising-a carrier and an oxaborole of general formula (1) or a salt thereof (hereinafter "biocide composition") with the proviso that when boronophthalide is the only oxaborole present the carrier is not an aviation fuel.

The carrier may be a material which shows little, if any, antimicrobial activity and may be, or include,, a medium which is susceptible to the growth of micro-organisms, such as bacteria or fungi. The carrier may be a solid but is preferably a liquid-medium and the biocide composition is preferably a solution, suspension or emulsion of the oxaborole in a liquid medium.

The carrier is generally selected so that the biocide composition is compatible with the medium to be protected. Thus, for example, if the medium to be protected is a solvent-based paint, lacquer or varnish the carrier is preferably a solvent, especially a non-polar solvent such as white spirits.

If the medium to be protected is a plastics material, the carrier is preferably a plasticiser or stabiliser typically used in the fabrication of plastics articles such as dioctylphthalate, dioctyladipate or epoxidised soya bean oil. If the medium to be protected is an aqueous medium, the carrier is preferably water or a water-miscible organic solvent or mixture thereof. Examples of suitable water-miscible organic solvents are acetic acid, N,N-dimethylformamide, dimethylsulphoxide, N-methyl-2-pyrrolidine, alcohols such as ethanol or glycols such as ethylene glycol, propylene glycol and dipropylene glycol and lower $C_{1-4}$-alkyl carbitols such as methyl carbitol. If the carrier is a solid, the composition may be a dry solid as described in EP 407024.

If the biocide composition is in the form of a suspension or emulsion, it preferably also contains a surface active agent to produce a stable dispersion or to maintain the non-continuous phase uniformly distributed throughout the continuous phase. Any surface active agent which does not adversely affect the biocidal activity of the compound of formula I may be used, for example alkylene oxide adducts of fatty alcohols, alkyl phenols, amines such as ethylene diamine and anionic surfactants such as adducts of naphthol sulphonates and formaldehyde.

The concentration of the oxaborole in the biocide composition is preferably up to a level at which the biocide composition is stable under the conditions of storage or transportation and is preferably from 1 to 50%, especially from 5 to 30% and more especially from 10 to 20% by weight relative to the total weight of the biocide composition.

As noted hereinbefore, many of the oxaboroles are new.

According to a further aspect of the invention there is provided a compound of formula (1)

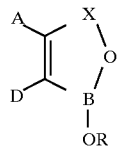

or a salt thereof wherein A, D, X and R are all as hereinbefore defined except for N-(1,3-dihydro-l-hydroxy-2,1-benzoxaborol-6-yl)-succinamic acid; 6-nitro-, 6-amino-, 7-methyl-, 6-(NN-dimethylamino)-, 5-(NN-dimethylamino)-, 4-bromo-, 6-methyl-, 5-bromo-6-methylol-1,3-dihydro-1-hydroxy-2,1-benzoxaborole; boronophthalide; 1-benzyloxy-, 1-cyclohexyloxy-, 1-ethoxy-1,3-dihydro-2,1-benzoxaborole; 1,1'-oxybis[1,3-dihydro-2,1-benzoxaborole]; 1,1'-oxybis[4-bromo-1,3-dihydro-2,1-benzoxaborole] and 3,7-dihydro-1,5-dihydroxy-1H, 3H-benzo[1,2-c: 4,5-c']bis[1,2]oxaborole.

Preferably A and D together with the carbon atoms to which they are attached form a fused phenyl ring which may itself be substituted as defined hereinbefore and preferably R is hydrogen or alkyl substituted by amino. It is also preferred that X is —$CH_2$—.

Preferably the fused phenyl ring contains a halogen atom in the 5 and/or 6 position of a benzoxaborole ring system, especially in the 5-position. Preferred halogens are fluorine and chlorine. Examples include 5-chloro and especially 5-fluoro benzoxaborole.

Other preferred oxaboroles are the O-esters obtainable by reacting the oxaborole with an aminoaliphatic carboxylic acid such as glycine or an alkanolamine such as ethanolamine, 3-aminopropanol or 4-aminobutanol.

According to a further aspect of the invention there is provided a compound of formula 3

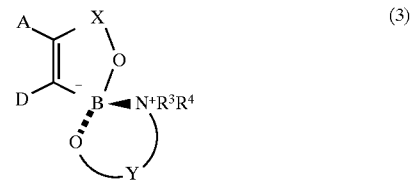

wherein A, D and X are as defined hereinbefore;

$R^3$ and $R^4$ are each, independently, hydrogen, optionally substituted $C_{1-18}$-alkyl or optionally substituted phenyl or $R^3$ together with Y or part of Y forms a 5-, 6- or 7-membered ring containing the nitrogen atom; and Y is an optionally substituted divalent alkylene linking group containing up to 18 carbon atoms.

The oxaboroles may be made by any method known to the art. Thus, the 1,3-dihydro-1-hydroxy-2,1-benzoxaboroles may be made by reacting an ortho-toluidine under Sandmeyer conditions to obtain an o-substituted halogeno toluene which is then reacted with magnesium or alkyl lithium such as butyl lithium in an inert solvent and the Grignard reagent or aryl lithium so formed is reacted with a borate ester such as tributyl borate to obtain a toluene boronic acid. This boronic acid is then reacted with a brominating agent such as N-bromosuccinimide in an inert solvent such as carbon tetrachloride to give a bromomethylbenzene boronic acid which is hydrolysed in alkali to give the hydroxymethyl analogue which is finally cyclised to give the benzoxaborole under acid conditions. This is method A. The preparation of o-bromomethylbenzeneboronic acids is described in JACS 1958 80 835.

Alternatively, an appropriate benzaldehyde is reacted with p-toluenesulphonylhydrazide in an inert solvent such as dry dichloromethane and the product is subsequently reacted with boron tribromide in the presence of a catalyst such as ferric or aluminium chloride and then cyclised to give a 1,2-dihydro-1-hydroxy-2-(4-methylphenyl-sulphonyl)-2,3, 1-benzodiazaborine. This is subsequently hydrolysed under alkaline conditions and then converted to the benzoxaborole under acid conditions. It is generally not necessary to isolate the intermediate diazaborine. This is method B and is described in Liebigs Ann. Chem. 1985 683.

Oxaboroles containing a fused aromatic ring can be made by reacting an aromatic compound containing a —$CH_2OH$ group with alkyl or aryl lithium and an organoborate in a dry inert organic liquid.

According to a still further aspect of the invention there is provided a process for making an oxaborole containing a fused aromatic ring which comprises reacting an aromatic compound containing a —$CH_2OH$ group with alkyl or aryl-lithium and an organo-borate in a dry inert organic liquid.

Preferably the fused aromatic ring is a fused phenyl ring and the aromatic compound containing a —$CH_2OH$ group is an optionally substituted benzyl alcohol.

Preferably the aromatic compound containing a —$CH_2OH$ group also contains one or more further substitutents which are ortho-lithiation activating groups since these allow for reaction under milder conditions. Such activating groups are preferably located in a position(s) other than ortho to the —CH$_2$OH group. Examples of activating groups are C$_{1-6}$-alkoxy, halogen such as chlorine and fluorine, substituted alkyl such as —CH$_2$OCH$_3$, —CH$_2$NT$_2$, —CH$_2$CH$_2$NT$_2$, substituted amino such as —NT$_2$, —NHCOT, —NHCO$_2$T and amides such as —SO$_2$NHT, —SO$_2$NT$_2$, —CONHT and —CONT$_2$ where T is aryl or alkyl. Preferably when T is aryl it is phenyl, and it is preferred that when T is alkyl it is C$_{1-6}$-alkyl.

An alkyl lithium compound is preferred which may be linear or branched and is preferably C$_{1-6}$-alkyl and especially C$_{1-4}$-alkyl such as butyl lithium.

The organic liquid is preferably an alkyl ether such as diethylether or preferably a cyclic-ether such as tetrahydrofuran.

The reaction may be carried out at temperatures up to the boiling point of the organic liquid. However, when the aromatic compound containing a —CH$_2$OH group also contains an ortho-lithiation activating group the reaction is preferably carried out below 0° C. and more preferably below −50° C. It is especially preferred that the reaction is carried out between −70° and −100° C.

The aromatic compound containing a —CH$_2$OH group may also carry further substitutents which do not react with the alkyl or aryl lithium compound.

The organo-borate is preferably an alkyl borate which may be linear or branched, more preferably a C$_{1-6}$-alkyl and especially a C$_{1-4}$-alkyl borate.

sec-Butyl lithium and n-butyl borate are preferred.

The reaction between the aromatic compound containing a —CH$_2$OH group and alkyl or aryl lithium is preferably carried out in the presence of a chelating agent. The preferred chelating agent is tetramethyleneethylenediamine.

Oxaboroles containing a fused aromatic ring can also be made by reacting an aromatic compound containing a —CH$_2$OH group and an ortho iodo or bromo group with alkyl or aryl lithium and an organo-borate.

According to a still further aspect of the invention there is provided a process for making an oxaborole containing a fused aromatic ring comprising reacting an aromatic compound containing a -CH$_2$OH group and an ortho iodo or bromo group with alkyl or aryl lithium and an organo-borate in an inert organic liquid.

Preferred reaction conditions are as defined for the aromatic compound containing a —CH$_2$OH group.

The boron esters of the oxaborole are typically made by reaction of an oxaborole of formula 1 where R is hydrogen with an appropriate amino-aliphatic carboxylic acid or preferably an alkanolamine in an inert solvent at 25°–125° C. when the boron ester is formed almost instantaneously. Preferably the inert solvent forms an azeotrope with water to facilitate removal of water formed when the alkanolamine is reacted with the oxaborole. It is especially preferred that the solvent is toluene. This is method C.

The oxaborole or compositions containing the oxaborole can be used for the treatment of various media to inhibit the growth of micro-organisms and are especially effective in providing anti-fungal activity.

As a further aspect of the present invention there is provided a method for inhibiting the growth of micro-organisms on, or in, a medium which comprises treating the medium with an oxaborole or a biocide composition containing an oxaborole.

The oxaborole can be used in conditions in which micro-organisms grow and cause problems. Systems in which micro-organisms cause problems include liquid, particularly aqueous, systems such as cooling water liquors, paper mill liquors, metal working fluids, geological drilling lubricants, polymer emulsions and especially surface coating compositions such as paints, varnishes and lacquers and more especially solid materials such as wood, plastics materials and leather.

The oxaboroles have been found particularly effective in inhibiting microbial degradation of plastics materials such as plasticised PVC and urethanes since they are not significantly adversely affected by the high temperatures commonly used in the fabrication of such articles. In this respect the benzoxazoles have been found especially effective, particularly those containing one or more halogen substituents in the fused phenyl ring of the benzoxaborole.

The oxaborole can be included in such materials to provide an anti-microbial effect. The amount of the compound is typically in the range from 0.00001 to 2.0% preferably from 0.0001 to 1% and especially from 0.0002 to 0.5% by weight of the compound relative to the system to which it is added. In certain cases, microbial inhibition has been obtained with from 0.0005% to 0.01% by weight of the oxaborole. Thus, in the case of plastics materials the oxaboroles have been found to inhibit microbial growth at an applied concentration of less than 0.05%, particularly less than 0.01% and especially less than 0.005% and more especially less than 0.001%.

The oxaborole may be the only antimicrobial compound used to protect the medium or it may be used together with one or more different oxaboroles or with one or more other compounds having antimicrobial activity. A mixture of anti-microbial compounds hereinafter referred to as a "biocide mixture" often has a broader anti-microbial spectrum and hence is more generally effective than the components of the mixture. The other antimicrobial compound or compounds may possess anti-bacterial, anti-fungal, anti-algal or other antimicrobial activity. The biocide mixture typically contains from 1 to 99% by weight, and preferably from 40 to 60% by weight, of an oxaborole relative to the total weight of an antimicrobially active compound, in the biocide mixture.

Examples of other antimicrobial compounds which may be used, together with the oxaborole are quaternary ammonium compounds such as N,N-diethyl-N-dodecyl-N-benzylammonium chloride; N,N-dimethyl-N-octadecyl-N-(dimethylbenzyl)ammonium chloride; N,N-dimethyl-N,N-didecylammonium chloride; N,N-dimethyl-N,N-didodecylammonium chloride; N,N,N-trimethyl-N-tetradecylammonium chloride; N-benzyl-N,N-dimethyl-N (C$_{12}$-C$_{18}$-alkyl)ammonium chloride; N-(dichlorobenzyl)-N, N-dimethyl-N-dodecylammonium chloride; N-hexadecylpyridinium chloride; N-hexadecylpyridinium bromide; N-hexadecyl-N,N,N-trimethylammonium bromide; N-dodecylpyridinium chloride; N-dodecylpyridinium bisulphate; N-benzyl-N-dodecyl-N,N-bis(beta-hydroxyethyl)ammonium chloride; N-dodecyl-N-benzyl-N, N-dimethylammonium chloride; N-benzyl-N,N-dimethyl-N-(C$_{12}$-C$_{18}$-alkyl)ammonium chloride; N-dodecyl-N,N-dimethyl-N-ethylammonium ethylsulphate; N-dodecyl-N, N-dimethyl-N-(1-naphthylmethyl)ammonium chloride; N-hexadecyl-N,N-dimethyl-N-benzylammonium chloride; N-dodecyl-N,N-dimethyl-N-benzylammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; 3-(3,4- dichlorophenyl)-1,1-dimethylurea; 3-(4-isopropylphenyl)-1,1-dimethylurea; tetrakis (hydroxy-methyl)acetylene diurea; 1-(hydroxymethyl)-5,5-dimethylhydantoin and imidazolidinylurea; amino compounds such as 1,3-bis(2-ethyl-hexyl)-5-methyl-5-amino-hexahydropyrimidine; hexamethylene-tetramine; 1,3-bis(4-amino-phenoxy)propane; and 2-[(hydroxymethyl)-amino]ethanol; imidazole derivatives such as 1[2-(2,4-dichloro-phenyl)-2-(2-propenyloxy)ethyl]-1H-imidazole; 2-(methoxycarbonyl-amino)-benzimidazol; 1-decyl-3-dodecyl-2-methylimidazolium bromide; dodecylbis(1-decyl-2-methyl-imidazolium)-dibromide; nitrile compounds such as 2-bromo-2-bromomethyl-glutaronitrile, 2-chloro-2-chloromethylglutaronitrile; 2,4,5,6-tetra-chloroisophthalodinitrile; thiocyanate derivatives such as methylene(bis)thiocyanate; tin compounds or complexes such as tributyltinoxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methyl-isothiazolin-3-one, benzisothiazolin-3-one; 2-methylbenzisothiazolin-3-one, 2-octylisothiazolin-3-one, 4,5-dichloro-2-octylisothiazolin-3-one; N-(2-ethylbutyl)benzisothiazolin-3-one); N-(n-hexyl)benzisothiazolin-3-one; thiazole derivatives such as 2-(thiocyanomethylthio)-benzthiazole and mercaptobenz-thiazole; nitro compounds such as tris(hydroxymethyl) nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl hemiformal, formaldehyde and glyoxal; amides such as chloracetamide; N,N-bis (hydroxymethyl)chloracetamide; N-hydroxymethyl-chloracetamide and dithio-2,2-bis(benzmethyl amide); guanidine derivatives such as poly (hexamethylenebiguanide) and 1,6-hexamethylene-bis[5-(4-chlorophenyl)biguanide]; imidazolium halides such as N,N'-didecyl-2-methylimidazolium bromide and 1,12-bis-(N-decyl-2-methylimidazolium)-dodecyl dibromide; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine, 6-chloro-2,4-diethylamino-s-triazine and 4-cyclopropylamino-2-methylthio-6-t-butylamino-s-triazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and 4-hydroxybenzoic acid and their salts and esters; phenol and derivatives thereof such as 5-chloro-2-(2,4-dichloro-phenoxy)phenol; thio-bis(4-chlorophenol) and 2-phenylphenol; sulphone derivatives such as diiodomethyl-paratolyl sulphone; 2,3,5,6-tetrachloro-4-(methylsulphonyl)pyridine and hexachlorodimethyl sulphone; thioamides such as dimethyldithiocarbamate and its metal complexes, ethylenebisdithiocarbamate and its metal complexes, and 2-mecaptopyridine-N-oxide and its metal complexes and imides such as trichloromethylmercaptophthalimide, fluorodichloromethylmercaptophthalimide, and trichloromethylmercaptotetrahydrophthalimide.

Further aspects of the present invention are described in the following illustrative examples in which all preparative details are given in parts by weight unless otherwise stated. The compounds were evaluated for their antimicrobial properties under sterile conditions using the test protocols described below.

Microtitre Screen Protocol for determining MIC For bacteria

An overnight culture (18 hours; 37° C.) of the appropriate micro-organism was prepared in nutrient broth to give approximately $10^9$ viable cells per 1 ml of culture. 20 μl of the culture was then transferred aseptically to 20 ml of the nutrient broth. 200 μl of this inoculum was then added to all vertical wells of a microtitre plate and 100 μl inoculum added to each subsequent row of vertical wells.

A 5000 ppm solution of the chemical under test was prepared in an appropriate solvent of which 20 μl was added to the first well of the second row of vertical wells to act as control. The contents of each well were mixed, 100 μl withdrawn and transferred to adjacent horizontal wells in that row. This process was repeated across each vertical row of wells to give a serial dilution of each compound under test ranging from 500 ppm to 0.25 ppm. The microtitre plate was then sealed and incubated at 25° C. for 42–48 hours. The minimum inhibitory concentration (MIC) was indicated by the well with lowest concentration showing no visible bacterial growth.

For Saccharomyces Cerevisiae

The culture was prepared as for bacteria except that Oxoid Malt broth was substituted for nutrient broth. Incubation was for 42 to 72 hours at 30° C.

For Fungi

The fungi were grown on a malt agar plate for one week at 25° C. and flooded with 2ml of sterile saline. Spores were released by careful agitation using a sterile loop. The spore suspension was poured into a Glass 25 ml Universal bottle. (Spore count approx $10^7$ ml$^{-1}$).

20 μl of the spore suspension was then added to 20 ml of malt broth and used to inoculate the microtitre plate. Dilutions were as described for the bacterial MIC and incubation was for 42–72 hours at 25° C.

Paint Film Protocol

This is identical to the Microtitre screen protocol except that the plates were incubated for 4 days and the organisms used were fungi that had been isolated from deteriorated paint film surfaces, namely Alternaria alternata (AA) PRA FS 4
Aureobasidium pullulans (AP) PRS FS 1
Cladosporium herbarum (CH) CMI 16203
Phoma violacia (PV) PRA FS 13
Stemphylium dendriticum (SD) PRA FS 15

EXAMPLE 1

Preparation of 5-chloro-1,3-dihydro-1-hydroxy-2,1-benzoxaborole (Method B)

a) Preparation of 3-chlorobenzaldehyde tosyl hydrazide

A solution of 3-chlorobenzaldehyde (15.56 parts; 0.109M; Aldrich) in methylated spirits (40 ml) was added slowly at below 10° C. to a stirred suspension of p-toluene-sulphonylhydrazide (20.7 parts; 0.108M) in methylated spirits (150 ml). The reaction mass was then stirred at 20° to 25° C. for 1 hour and then heated at 60°–70° C. for 1½ hours when the reactants and products dissolved. The solvent was then removed by rotary evaporation and the product was obtained as a solid which was slurried with ether and washed with n-hexane. Yield=27.2 parts (81.5% theory) mpt 122°–3° C.

Elemental analysis

Theory 54.5%C; 4.2%H; 9.1%N

Found 54.5%C; 4.3%H; 9.1%N

Proton NMR (CDCl$_3$:ppm)

8.5, s, 1H(—NH—); 7.9, d, 2H(Tosyl aromatic); 7.7,s, 1H(CH═N); 7.5, s, 1H(aromatic); 7.2–7.4, m, 5H(Tosyl aromatic); 2.3, s, 3H(—CH$_3$)

b) Preparation of title compound

A suspension of anhydrous ferric chloride catalyst (0.75 parts, Fisons) in dry dichloromethane (20 ml) was added at 20° to 25° C. simultaneously with boron tribromide (25 parts, 0.1M, Aldrich) in dry dichloromethane (100 mls) to a stirred suspension of the hydrazide from a) above (10.18 part, 0.033M) in dry dichloromethane (160 mls) under a nitrogen blanket. The reactants were then stirred under reflux and the evolved hydrogen bromide trapped under aqueous sodium hydroxide. After 3 hours stirring at reflux, the reactants were allowed to stand at 20°–25° C. for 48 hours and then stirred under reflux for a further 4 hours. The reaction mass was then cooled and the solvent removed by rotary evaporation. The solid obtained was then stirred under reflux with 2N sodium hydroxide solution (160 ml) for 3 hours. The brown aqueous suspension was extracted with dichloromethane (50 ml), screened and then acidified to about pH 2 by addition of 2N hydrochloric acid. The solid was filtered, slurried with dichloromethane (400 ml) and then washed with a saturated solution of sodium bicarbonate followed by water. Yield=24 parts (43% theory). The solid was slurried in hot dichloromethane and filtered to give 0.36 parts oxaborole mp 140°–45° C. The dichloromethane solution was cooled and the solid filtered giving a further 0.35 parts oxaborole mp 146°–8° C. The solids were combined and recrystallised from methylated spirits.

Yield=0.51 parts (9.2% theory) mp 150°–4° C.

Elemental Analysis

Theory 49.8%C, 3.5%H, 21.06%Cl

Found 49.5%C, 3.5%H, 21.0%Cl

Proton NMR (CDCl$_3$) ppm 9.3, s, 1H(—OH); 7.5, d, s, d, 3H(aromatic); 5.0, s, 2H(—CH$_2$—O).

EXAMPLE 2

Preparation of the ethanolamine ester of boronophthalide (Method C)

Boronophthalide (0.22 part, 0.00164M) was dissolved in toluene (40 ml) at 80° C. and ethanolamine (0.1 part, 0.00164M) added slowly. The ester formed immediately. Toluene (50 ml) was added, and the reactants heated to reflux to dissolve the ester. After screening, the product separated on cooling as a pale solid 0.15 part (52% theory) mp 214°–216° C.

Elemental Analysis

Theory 61%C, 6.8%H, 7.9N

Found 60.3%C, 6.7%H, 7.6%N

EXAMPLE 3

Preparation of 3-aminopropanol ester of boronophthalide

This was prepared as described in example 2 but using boronophthalide (0.15 part, 0.00112M) and 3-aminopropanol (0.084 part, 0.00112M, Aldrich). The product was obtained as a colourless solid by recrystallisation from toluene/100°–120° C. petroleum ether.

Yield=0.18 part (84% theory) mp=174°–6° C.

Elemental Analysis

Theory 62.80C; 7.3%H; 7.3%N

Found 64.5%C; 7.5%H; 7.1%N

EXAMPLES 4–14

The MIC of the following boronophthalide derivatives was determined using the microtitre screen protocol described hereinbefore.

In these examples two fungi and two bacteria were used namely *Saccharomyces cerevisiae* NCYC 124 (SC), *Asperaillus niger* CMI 17454 (AN), *Pseudomonas aeruginosa* NCIB 10421 (PA) and *Staphylococcus aureus* NCIB 9518 (SA).

The results are given in Table 1 below.

TABLE 1

| | | MIC date (ppm) organism | | | |
|---|---|---|---|---|---|
| Example | Substituent | SC | AN | PA | SA |
| 4 | — | 0.5 | 0.25 | >50 | 62 |
| 5 | 6 Cl— | 2 | 2 | N | 62 |
| 6 | 5 PhO— | 31 | 16 | N | 31 |
| 7 | 5 tert Bu— | 125 | 62 | N | 31 |
| 8 | 5 F— | <0.25 | <0.25 | 125 | 31 |
| 9 | 5,6 fused Ph | 31 | 16 | N | 16 |
| 10 | 4,5 fused Ph | 16 | 16 | N | 62 |
| 11 | 3 Ph— | 16 | 31 | N | 125 |
| 12 | 5 Cl— | 0.5 | <0.25 | N | 62 |
| 13 | 5 CF$_3$— | 8 | 0.25–0.5 | 125 | 62 |
| 14 | 5 Br— | 8 | 1 | N | 125 |

Footnote to Table 1
N = No activity at 100 ppm level
SC, AN, PA, SA are as described in the microtitre screen

EXAMPLES 15 to 18

A 0.1% (w/w) solution of the fungicides under test was prepared in 50/50 dioctylphthalate and dioctyladipate. Aliquots of 0.125, 0.25, 0.5, 2.0 and 3.0 mls of each solution (to give 1.25, 2.5, 5, 20 and 30 ppm fungicide) was adjusted in volume to 3 mls by adding the dioctylphthalate/adipate mixture and then made up to 100 ml with Potato Dextrose Tryptone soya agar and homogenised. Plates were cast in petri dishes and allowed to set. Each plate was then inoculated, using a multi-point applicator, with a 10$^5$ spore suspension of AP, FS, PF and SB and a 10$^5$ colony suspension of SW. The plates were incubated at 20° C. for 4 days and the MIC value determined. The results are given in Table 2 below.

TABLE 2

| | | Fungi | | | | |
|---|---|---|---|---|---|---|
| Example | Substituent | AP | FS | PP | SB | SW |
| 15 | — | <1.25 | <1.25 | <2.25 | <1.25 | <1.25 |
| 16 | 6 Cl— | 20 | 20 | 2.5 | 2.5 | 2.5 |
| 17 | 5 Cl— | <1.25 | <1.25 | <1.25 | <1.25 | 5 |
| 18 | 5 F— | <1.25 | <1.25 | <1.25 | <1.25 | <1.25 |

TABLE 2-continued

| | | Fungi | | | | |
|---|---|---|---|---|---|---|
| Example | Substituent | AP | FS | PP | SB | SW |
| A | SK | 2.5 | 20 | <1.25 | 2.5 | 2.5 |
| B | DS | 60 | 80 | 4.0 | 2.5 | 2.5 |

Footnote to Table 2
SK = 2-n-octylisothiazolin-3'-one
DS = 2,3,5,6-tetrachloro-(4-methylsulphone)pyridine
AP = *Aureobasidium pullulans*
FS = *Fusarium solani*
PP = *Pepicillium pinophylum*
SB = *Scopulariopsis brevicaulis*
SW = *Streptoverticillium waksmanii*

EXAMPLES 19–22

The MIC of the following benzoxaborole derivatives was determined using the paint film protocol described hereinbefore. The values obtained are given in Table 3 below.

TABLE 3

| | | Organism | | | | |
|---|---|---|---|---|---|---|
| Example | Substituent | PV | CH | AA | AP | SD |
| 19 | — | 1 | 4 | 2 | 2 | 1 |
| 20 | 5 F— | <0.25 | 0.5 | <0.25 | <0.25 | <0.25 |
| 21 | 5 Cl— | <0.25 | 0.5 | <0.25 | <0.25 | <0.25 |
| 22 | 5 Br— | 2 | 4 | 2 | 1 | 2 |

TABLE 3-continued

| | | Organism | | | | |
|---|---|---|---|---|---|---|
| Example | Substituent | PV | CH | AA | AP | SD |
| C | SK | 1 | 8 | 0.5 | <0.25 | 8 |
| D | TP | 0.8 | 0.8 | 0.4 | 0.4 | 0.8 |

Footnote to Table 3
SK = 2-n-octylisothiazolin-3-one
TP = iodopropynylbutylcarbamate

Preparative Examples 23 to 58

Example 1 a) and b) was repeated using the equivalent weight of benzaldehyde and 3-fluorobenzaldehyde in place of the 3-chlorobenzaldehyde used in Example 1a to obtain the analogous 1,3-dihydro-1-hydroxy-2,1-benzoxaborole derivatives. These benzoxaborole derivatives were then reacted with an alkanolamine as described in Example 2 by replacing the ethanolamine with the equivalent amount of alkanolamine.

The benzoxaborole esters obtained have formula 2

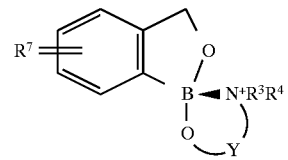

The elemental analysis and/or melting points of the compounds obtained are given in Table 4 below.

TABLE 4

| | | | | | | Elemental Analysis (%) | | | | | |
|---|---|---|---|---|---|---|---|---|---|---|---|
| Ex | $R^7$ | $R^3$ | $R^4$ | Y | mp °C. | Found | | | Theory | | |
| 23 | H | H | H | —(CH$_2$)$_2$— | 214–216 | 60.3 C | 6.7 H | 7.6 N | 61.0 C | 6.8 H | 7.9 N |
| 24 | H | H | H | —(CH$_2$)$_3$— | 174–176 | 64.5 C | 7.5 H | 7.1 N | 62.8 C | 7.3 H | 7.3 N |
| 25 | H | H | H | —(CH$_2$)$_4$— | 161–163 | 64.9 C | 8.1 H | 7.0 N | 64.4 C | 7.8 H | 6.8 N |
| 26 | 5-Cl | H | H | —(CH$_2$)$_3$— | 196–199 | | | | | | |
| 27 | 5-Cl | H | H | —(CH$_2$)$_4$— | 169–171.5 | | | | | | |
| 28 | 5-Cl | Me | H | —(CH$_2$)$_2$— | 143–148 | | | | | | |
| 29 | 5-Cl | H | H | —CH$_2$—CH(CH$_3$)— | 191–194 | | | | | | |
| 30 | 5-Cl | H | H | —CH(CH$_3$)—CH$_2$— | 206–210 | | | | | | |
| 31 | 5-Cl | H | H | —CH$_2$—C(CH$_3$)$_2$— | 172–175 | | | | | | |
| 32 | H | Me | H | —(CH$_2$)$_2$ | 167–169 | 62.4 C | 7.4 H | 7.2 N | 62.8 C | 7.3 H | 7.3 N |
| 33 | H | H | H | —CH$_2$C(CH$_3$)$_2$— | 176–178 | 61.5 C | 7.4 H | 5.3 N | 64.4 C | 7.8 H | 6.8 N |
| 34 | 5-F | H | H | —(CH$_2$)$_3$— | 186–187 | 62.6 C | 6.1 H | 5.5 N | 62.6 C | 6.2 H | 6.7 N |
| 35 | H | Me | Me | —(CH$_2$)$_2$— | | 61.5 C | 7.4 H | 5.3 N | 61.7 C | 7.9 H | 6.5 N |
| 36 | 5-F | Me | H | —(CH$_2$)$_2$— | 184–192 | 57.0 C | 6.0 H | 7.3 N | 57.4 C | 6.2 H | 6.7 N |
| 37 | 5-F | H | H | —(CH$_2$)$_2$— | 232–234 | 55.0 C | 5.5 H | 7.1 N | 55.4 C | 5.6 H | 7.2 N |
| 38 | 5-F | H | H | —CH$_2$—C(CH$_3$)$_2$— | 132–134 | 57.9 C | 6.7 H | 6.1 N | 58.0 C | 6.8 H | 6.2 N |
| 39 | 5-F | H | H | —(CH$_2$)$_4$— | 163–165 | 58.6 C | 6.8 H | 6.5 N | 59.2 C | 6.7 H | 6.3 N |
| 40 | H | tBu | H | —(CH$_2$)$_2$— | 141–143 | 62.4 C | 8.3 H | 4.7 N | 62.2 C | 8.8 H | 5.6 N |
| 41 | H | Et | H | —(CH$_2$)$_2$— | 178–180 | 64.2 C | 7.2 H | 6.7 N | 64.4 C | 7.9 H | 6.8 N |
| 42 | H | nPr | H | —(CH$_2$)$_2$— | 166–168 | 64.9 C | 7.1 H | 6.4 N | 64.8 C | 8.3 H | 6.3 N |
| 43 | H | nBu | H | —(CH$_2$)$_2$— | 159–161 | 66.4 C | 7.6 H | 5.9 N | 67.0 C | 8.6 H | 6.0 N |
| 44 | H | nPe | H | —(CH$_2$)$_2$— | 135–137 | 67.0 C | 6.3 H | 5.7 N | 68.0 C | 9.0 H | 5.7 N |
| 45 | H | H | H | —CH(CH$_3$)—CH$_2$— | 213–216 | 62.6 C | 7.0 H | 7.2 N | 62.8 C | 7.3 H | 7.3 N |
| 46 | 5-Cl | H | H | —CH—(CH$_2$CH$_3$)CH$_2$— | 213–214.5 | | | | | | |
| 47 | 5-Cl | H | H | —CH$_2$—CH(CH$_2$CH$_3$)— | 187.5–169 ' | | | | | | |
| 48 | H | H | H | —CH$_2$CH(CH$_3$)— | 173–175 | 64.5 C | 7.5 H | 6.4 N | 62.B C | 7.3 H | 7.3 N |
| 49 | H | H | H | —CH$_2$CH(CH$_2$CH$_3$)— | 20S–207 | 64.4 C | 7.5 H | 6.8 N | 64.4 C | 7.9 H | 6.6 N |
| 50 | H | H | H | —CH(CH$_2$CH$_3$)CH$_2$— | 207–210 | 64.2 C | 7.9 H | 7.1 N | 64.4 C | 7.9 H | 6.6 N |
| 51 | H | H | H | —CH$_2$CH((CH$_2$)$_3$CH$_3$)— | 166–191 | 66.8 C | 8.7 H | 6.4 N | 67.0 C | 6.6 H | 6.0 N |
| 52 | H | H | H | —CH$_2$CH(CH$_2$CH(CH$_3$)$_2$)— | 204–207 | 66.6 C | 7.6 H | 6.0 N | 67.0 C | 6.6 H | 6.0 N |
| 53 | H | H | H | —CH$_2$CH((CH$_2$)$_2$CH$_3$)— | 210–213 | 66.4 C | 6.4 H | 6.5 N | 65.6 C | 8.3 H | 6.4 N |
| 54 | H | H | H | —CH$_2$CH((CH$_2$)$_2$SCH$_3$)— | 174–17S | 57.4 C | 6.1 H | 5.8 N | 57.4 C | 7.2 H | 5.6 N |
| | | | | | | | 13.0 S | | | 12.8 S | |

TABLE 4-continued

| Ex | R[7] | R[3] | R[4] | Y | mp °C. | Found | | | Theory | | |
|---|---|---|---|---|---|---|---|---|---|---|---|
| | | | | | | \multicolumn{3}{c}{Elemental Analysis (%)} | | | |
| 55 | 5-F | Et | H | —(CH$_2$)$_2$— | 186–169 | 59.2 C | 6.6 H | 6.3 N | 59.2 C | 6.1 H | 6.1 N |
| 56 | 5-F | H | H | —CH$_2$CH(CH$_2$CH$_3$)— | 212–214 | 59.0 C | 6.5 H | 6.2 N | 59.2 C | 6.6 H | 6.3 N |
| 57 | 5-F | H | H | —CH(CH$_2$CH$_3$)CH$_2$— | 205–208 | 56.3 C | 6.6 H | 6.2 N | 59.2 C | 6.6 H | 6.3 N |
| 58 | 5-F | Pr | H | —(CH$_2$)$_2$— | 162–184 | 60.8 C | 7.4 H | 5.8 N | 60.6 C | 7.2 H | 5.9 N |

Preparative Examples 59–78 (except 65 and 71)

These oxaboroles where prepared by an analogous method to that described in Example 1 a) and b) by replacing the 3-chlorobenzaldehyde with an equivalent amount of appropriate aldehyde. The benzoxaborole derivatives obtained have general formula

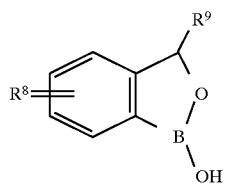

The elemental analysis and/or melting points of such compounds are listed in Table 5 below.

and washed with ether. The hydrazone was obtained as a white powder (24.0 parts; 83% theory) mp 184°–6° C.
Proton NMR Analysis
2.44 (s, 3H), 7.0–7.18 (m, 2H), 7.27–7.38 (m, 5H)
2.42–2.48 (m, 2H), 7.48–7.55 (m, 4H), 7.56 (s, H)
7.86 (d, 2H).

b) Preparation of Diazaborine derivative

Anhydrous ferric chloride (0.75 parts) was suspended in dry dichloroethane (75 ml) and solutions of boron tribromide (131 ml of M solution in dichloromethane, 0.131M ex Aldrich) and the hydrazone from (a) above (15.0 parts, 0.043M in dry dichloroethane, 200 ml) added simultaneously at 20° C. over 15 mins with stirring under nitrogen. The temperature rose by about 2° C. The dark red reaction mix was stirred at reflux for 4½ hours to remove the hydrogen bromide.

The reactants were then cooled and drowned into ice (500 parts) and water (500 parts). The organic phase was sepa-

TABLE 5

| Example | R[8] | R[9] | mp °C. | Found | | | Theory | | |
|---|---|---|---|---|---|---|---|---|---|
| | | | | \multicolumn{3}{c}{Elemental Analysis (%)} | | | |
| 59 | 6-Cl | H | 156–158 | 49.5 C | 3.5 H | 21.0 N | 49.8 C | 3.5 H | 21.0 N |
| 60 | 5-PhO | H | 101–105 | | | | | | |
| 61 | 5-C(CH$_3$)$_3$ | H | 119–123 | | | | | | |
| 62 | 4,5 fused Ph | H | 137–139.5 | | | | | | |
| 63 | 5,6 fused Ph | H | 161–163.5 | | | | | | |
| 64 | 5-F | H | 127–129 | 54.9 C | 4.2 H | | 55.2 C | 3.9 H | |
| 65 | H | Ph | 145–147 | | | | | | |
| 66 | 5-Cl | H | 150–155 | 49.9 C | 3.5 H | 20.8 N | 49.8 C | 3.5 H | 21.0 N |
| 67 | 5-CF3 | H | | 47.6 C | 3.1 H | | 47.5 C | 2.9 H | |
| 68 | 5-Br | H | | 39.4 C | 2.7 H | 39.6 Br | 39.4 C | 2.8 H | 37.6 Br |
| 69 | 4-F | H | | 54.8 C | 4.2 H 8.9 F | 6.9 B | 55.2 C | 3.95 H 12.5 F | 7.2 B |
| 70 | 6-F | H | | 54.5 C | 4.1 H 8.5 F | 7.1 B | 55.2 C | 3.95 H 12.5 F | 7.2 B |
| 71 | H | —CN | 114–115 | 59.0 C | 3.5 H | 8.6 N | 60.3 C | 3.8 H | 8.8 N |
| 72 | 4-CH$_3$, 5-F | H | 162–163 | 57.4 C | 4.4 H | 5.9 B | 57.8 C | 4.8 H | 6.6 B |
| 73 | 5,6 diF | H | 148–151 | 49.2 C | 3.0 H | 6.2 B | 49.4 C | 2.9 H | 6.4 B |
| 74 | 5-CH$_3$O | H | 122–124 | | | | 58.5 C | 5.4 H | 6.7 B |
| 75 | 7-F | H | 132–134 | | | | 55.0 C | 4.0 H | 7.1 B |
| 76 | 4,7 diF | H | | | | | | | |
| 77 | 6,7 diF | H | | | | | | | |
| 78 | 5,7 diF | H | | | | | | | |

Preparative Example 65

Preparation of 3-phenyl-1,3-dihydro-1-hydroxy-2,1-benzoxaborole a) Preparation of benzophenone p-toluenesulphonylhydrazone Benzophenone (15.0 parts, 0.082M ex Fluka) was stirred at reflux with p-toluene sulphonylhydrazine (15.33 parts, 0.082M ex Aldrich) in ethanol (125 ml) for 10 hours. Gradually a pale yellow solution formed from which the hydrazone gradually precipitated. After cooling to 20° C., diethylether (20 ml) was added and the hydrazone filtered rated and extracted with aqueous sodium hydroxide solution. The aqueous layer was then separated and the pH adjusted to pH 3 by addition of concentrated hydrochloric acid. This aqueous layer was extracted with dichloromethane which was then separated, dried over magnesium sulphate and the solvent removed to give the product as a cream solid. Yield=3.83 parts (24% theory) mp 239°–42° C.
Proton NMR Analysis
2.44 (s, 3H), 7.33 (d, 2H), 7.37–7.52 (m, 5H), 7.44 (s, H),
7.55–7.71 (m, 3H), 7.95 (d, 2H), 8.25–8.35 (m, H).

c) Preparation of title compound

The diazaborine from (b) (2.6 parts) was stirred at reflux in 10% aqueous potassium hydroxide solution (100 ml) containing ethanol (50 ml) for 4½ hours. The solution was then cooled, washed with dichloromethane and the pH adjusted to pH 3 with concentrated hydrochloric acid. A suspension formed which was extracted into dichloromethane. After removal of the solvent, a pale cream solid was obtained which was found to be a mixture of starting material and product. This was purified by preparative column chromatography using a silica column developed with dichloromethane.

After removing the solvent by evaporation, the product was obtained as a white solid (0.49 parts; 24% theory) mp=145°–7° C.

Proton NMR Analysis 6.14 (s, H), 7.15 (d, H), 7.21–7.46 (m, 7H), 7.83 (d, H), 8.51 (s, H).

Preparative Example 71

Preparation of 3-cyano-1,3-dihydro-1-hydroxy-2,1-benzoxaborole a) Preparation of 2-formylphenylboronic acid (Ref JACS 86 1964 p435)

o-Tolyl boronic acid (10 parts; 0.0714M ex Aldrich) and N-bromosuccinimide (30.13 g; 0.169M ex Aldrich) were dried at 110° C. for 16 hours. Both these reactants were added to carbon tetrachloride (450 ml) and 50 ml of the solvent distilled off to remove any remaining water. Benzoyl peroxide (1.5 parts) was added and the reactants stirred under reflux for 6 hours. After cooling, cyclohexene (1.25 parts) was added to remove any bromine and the solution screened to remove succinimide. The product was then extracted with 15% aqueous potassium hydroxide solution (4×35 ml). These aqueous extracts were combined and acidified to about pH 4 with concentrated hydrochloric acid. The product was then extracted into diethylether (3×200 ml). The combined ether extracts were then dried over magnesium sulphate and the ether evaporated. Finally, the product was recrystallised from water. Yield=1.69 parts (15.3% theory) mp 122°–4° C.

Elemental Analysis

Found 55.3% C, 4.7% H

Theory 56.0% C, 4.7% H b) Preparation of title compound (Ref JOC 29 1964 p2172)

2-formyl phenyl boronic acid (1.0 parts, 0.007M) was added to an aqueous solution of sodium cyanide (0.35 parts) in water (20 ml) at 20° C. with stirring. After 15 mins the reactants were cooled to 5° C. and carefully neutralised to pH 5 with concentrated hydrochloric acid. The resultant white precipitate was filtered and recrystallised from water (25,ml). The product was dried over calcium chloride. Yield=0.29 parts (26% theory) mp=114°–5° C.

Elemental Analysis

Found 59.0%, 3.5% H, 8.6% N

Theory 60.3%, 2.8% H, 8.8% N.

Preparative Examples 79 and 80

Example 2 was repeated except that the ethanolamine was replaced by an equivalent amount of 8-hydroxyquinoline to give the benzoxaborole of Example 79. Example 80 was obtained by replacing the boronophthalide of Example 79 with the equivalent amount of the 5-fluoro analogue. The analytical data and/or melting point is given in Table 6 below for the benzoxaborole of formula

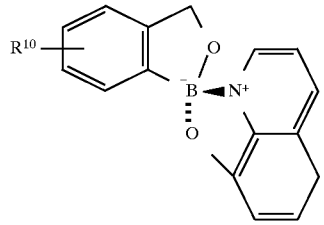

TABLE 6

| Example | $R^{10}$ | mp °C. | Elemental Analysis (%) Found | Elemental Analysis (%) Theory |
|---|---|---|---|---|
| 79 | H | 189–190 | 73.4 C 4.4 H 5.4 N | 73.6 C 4.6 H 5.4 N |
| 80 | F | 118–119 | | 68.8 C 3.9 H 5.0 N |

Preparative Examples 81–90

Preparative examples 23–58 were again repeated using equivalent amounts of various aldehydes and alkanolamines to obtain further benzoxaborole esters of formula 2

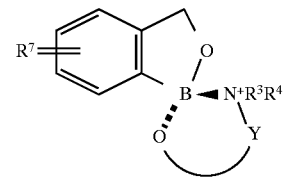

The melting points of these compounds are given in Table 7 below.

TABLE 7

| Example | $R^7$ | $R^3$ | $R^4$ | Y | mp °C. |
|---|---|---|---|---|---|
| 81 | 5 Cl | H | H | —(CH$_2$)$_2$— | 205–208 |
| 82 | 5 PhO— | H | H | —(CH$_2$)$_2$— | 175–179 |
| 83 | 5 C(CH$_3$)$_3$ | H | H | —(CH$_2$)$_2$— | 165–168 |
| 84 | 5 Cl | H | H | —CH(Ph)CH$_2$— | 203–206.5 |
| 85 | 5 Cl | H | H | —CH$_2$CH(Ph)— | 59–66 |
| 86 | 5 Cl | H | H | —COCH$_2$— | 216–219 |
| 87 | 5 Cl | H | H | —CH$_2$CH(CH$_2$Ph)— | 202.6–205 |
| 88 | 4,5 fused Ph | H | H | —(CH$_2$)$_2$— | 228–230 |
| 89 | 5,6 fused Ph | H | H | —(CH$_2$)$_2$— | 204–206 |
| 90 | 5 Cl | H | H | —CH$_2$-N(pyrrolidine) | 212–213 |

Preparative Example 91

Preparation of 5-methoxy-1,3-dihydro-1-hydroxy-2,1-benzoxaborole 2-bromo-5-methoxybenzylalcohol (6.5 parts; 0.03M) was dissolved in dry THF (100 ml) and cooled to −78° C. n-Butyl-lithium (26.4 ml of a 2.5M solution in hexanes ex Aldrich, 0.066M) was added over 20 minutes with stirring under a nitrogen blanket and keeping the temperature below −60° C. After stirring for a further hour at −70° C. HPLC showed the reaction to be incomplete with 20% starting material remaining. A further aliquot of n-butyl-lithium in hexanes (5 ml; 0.0125M) was added and the reactants allowed to warm to −50° C.

Tributylborate (17.8 ml; 0.066M) was then added at between −70° and −50° C. with stirring under a nitrogen blanket and the reactants allowed to warm to about 20° C. Water (20 ml) was added and the pH adjusted to 10 with hydrochloric acid. After washing with diethylether, the pH of the aqueous phase was adjusted to pH 1–2 with hydrochloric acid and washed with diethyl ether. The ether extract was washed with aqueous saturated brine, dried over anhydrous magnesium sulphate and the ether evaporated to leave the product as a pale oil (3.7 parts). This was slurried with water containing a little methanol whereupon a pinkish-white solid separated which was filtered, washed with water and dried (2.0 parts) mp=110°–115° C. after recrystallisation from aqueous methanol.

Preparative Example 92

Preparation of 7-fluoro-1,3-dihydro-1-hydroxy-2,1-benzoxaborole 3-fluorobenzyl alcohol (3.5 parts; 0.028M) was stirred in THF (100 ml) containing tetramethylene ethylenediamine (10.2 ml; 0.067M). After cooling to −78° C., sec-butyl-lithium (77 ml of 0.8M solution in cyclohexane ex Aldrich; 0.061M) was slowly added over 45 min at between −78° and −65° C. with stirring under a nitrogen blanket. After 1 hour at −78° C., tributyl borate (16.78 ml; 0.061M) was added dropwise and the reactants stirred under nitrogen for 16 hrs allowing the temperature to slowly raise to 20° C. Dilute hydrochloric acid was added to bring the pH to about 12 and the aqueous phase separated and washed with diethylether. The pH of the aqueous phase was then acidified to about pH 2 with hydrochloric acid and extracted with ether (3×100 ml). These ether extracts were washed with saturated brine, dried over magnesium sulphate and the ether evaporated whereupon the product separated as a pale solid (2.6 parts; 62% theory) mp=132°–134° C. after recrystallisation from aqueous methanol.

Preparative Example 93

Preparation of

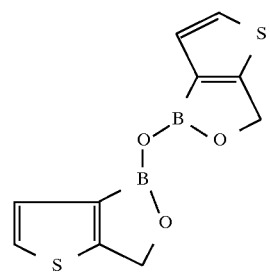

a) Preparation of 3-bromo-2-formylthiophene Ref Acta Chem Scand 22 (1968) 4 1354

2,3-dibromothiophene (14 parts, 0.058M ex Lancaster Chemicals) was weighed into a reaction vessel equipped with a rubber septum. Dry diethyl ether (112 mls) was added by syringe through under a nitrogen blanket and cooled to −70° C. n-Butyl lithium (26.8 mls of 2.5M solution in hexanes ex Aldrich) was slowly added over 20 mins. After stirring at −70° C. for ½ hour, dimethylformamide (6.3 parts) in diethyl ether was added over 5 mins. The reactants were allowed to warm to 20° C., then 100 mls water was added with stirring. The ether solution was then washed with N hydrochloric acid, aqueous bicarbonate and water. The ether solution was then dried over magnesium sulphate and the ether evaporated to leave an orange/brown oil (12.32 parts). This oil was distilled at 0.05 mm Hg and 680C to give a straw-coloured oil (4.5 parts). This oil was dissolved in dichloromethane and evaporated onto silica. This silica was formed into a column and the product separated by flash chromatography. The silica column was developed by washing with hexane containing increasing amounts of dichloromethane. The product was eluted in fractions containing from 10–30% dichloromethane in hexane.

Yield=4.05 parts.

Elemental Analysis

Found 32.0% C, 1.8% H, 16.7% S

Theory 31.4% C, 1.6% H, 16.8% S b) Preparation of 2-(3-bromo-2-thienyl)-1,3-dioxolane 3-bromo-2-formylthiophene (3.89 parts, 0.02M) was heated at reflux with dry ethyleneglycol (1.6 parts) toluene (25 parts) and p-toluene sulphonic acid (0.1 parts) in a vessel equipped with a Dean and Stark separator for 16 hours. The reactants were then cooled and evaporated into silica. The silica was formed into a column which was then developed by elution with hexane containing increasing amounts of dichloromethane. The product was obtained from fractions containing 10–60% dichloromethane as a pale straw-coloured oil (4.42 parts).

Elemental Analysis

Found 35.6% C, 3.1% H, 13.6% S

Theory 35.8% C, 3.0% H, 13.7% S c) Preparation of 2-formyl-3-thiopheneboronic acid Butyl lithium (7.9 ml of 2.5M solution in hexanes ex Aldrich) was slowly added to a solution of the dioxolane from (b) (4.28 parts, 0.018M) in dry diethylether with stirring at −70° C. under a nitrogen blanket. After stirring for 15 mins butyl borate (6 mls ex Aldrich) dissolved in ethylether (20 ml) was slowly added at −70° C. The reactants were stirred for a further 4 hours at -700C and then warmed to 20° C. 25 ml N hydrochloric acid was added and the reactants stirred for 1 hour at 20° C. The ether layer was then separated and extracted with N aqueous sodium carbonate solution (3×10 ml). This aqueous carbonate solution was slowly acidified whereupon the product separated and was filtered and dried.

Yield=0.89 parts.

Elemental Analysis

Found 36.6% C, 3.0% H, 19.6% S

Theory 38.5% c, 3.2% H, 20.5% S d) Preparation of title compound

The boronic acid from (c) (0.5 parts, 0.0032M) was dissolved in ethanol and sodium borohydride (30 mg ex Aldrich) added with stirring at 20° C. After 30 mins the reaction mass was evaporated onto silica which was formed into a column and developed with hexane containing increasing amounts of dichloromethane and then dichloromethane containing increasing amounts of methanol. The product was obtained from fractions of dichloromethane containing 3–4% methanol. After evaporating the solvent, the product was recrystallised from toluene.

Yield=0.13 part mp 203°–4° C.

Elemental Analysis

Found 45.5% C, 3.2% H, 23.3% S

Theory 45.8% c, 3.1% H, 26.4% S

The microbiological test data for this compound is

| AN | CA | AP | GR | PP | EC | PA | SA | BS |
|----|----|----|----|----|----|----|----|----|
| N  | N  | N  | N  | N  | N  | N  | 100 | 25 |

The legands are explained in the footnote to Table 8.

Microbiological Examples 23 to 58

The MIC of the following benzoxaborole esters was determined against the micro-organisms indicated in Table 8 for the compounds of formula

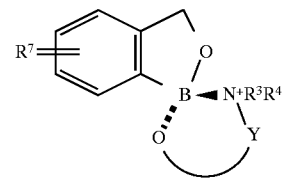

$R^7$ represents one or more substituents in the phenyl ring.

The test method employed was as follows.

The bacterial inoculum consisted of 24 hour cultures of the organisms grown in Oxoid Nutrient broth, subcultured daily and incubated at 37° C.

Spore suspensions of each of the test fungi were prepared in the following manner. To 250 ml conical flasks containing well sporulating cultures of the fungi, growing on Oxoid Malt extract agar, a number of sterile 3 mm glass beads and approximately 50 ml of a sterile solution of 0.01% v/v of polyoxyalkylene (20) sorbitan mono-oleate (ex ICI as Tween 80 —Tween is a registered trademark) in water were added. Each flask was swirled so that the beads removed the spores and the resulting suspension was poured into a sterile 100 gm medical flat bottle containing approximately 50 ml of the sterile 0.01% v/v solution of Tween 80. The suspension was storable for up to four weeks at 40° C.

In the microbiological testing, the oxaborazoles were tested at 5, 25 and 100 ppm against the bacteria, yeast and fungi listed in the footnote to Table 8.

TABLE 8

|         |       |       |       |                  | Fungi |    |    |    |    | Bacteria |    |    |    |
|---------|-------|-------|-------|------------------|-------|----|----|----|----|----|----|----|----|
| Example | $R^7$ | $R^3$ | $R^4$ | Y                | AN    | CA | AP | GR | PP | EC | PA | SA | BS |
| 23 | H    | H           | H    | —(CH$_2$)$_2$—       | 5 | 5 | 5 | 5 | 5 | 25  | 25  | 25  | 25 |
| 24 | H    | H           | H    | —(CH$_2$)$_3$—       | 5 | 5 | 5 | 5 | 5 | 25  | 25  | 25  | 25 |
| 25 | H    | H           | H    | —(CH$_2$)$_4$—       | 5 | 5 | 5 | 5 | 5 | 25  | 25  | 25  | 25 |
| 26 | 5-Cl | H           | H    | —(CH$_2$)$_3$—       | 5 | 5 | 5 | 5 | 5 | 25  | 25  | 100 | 25 |
| 27 | 5-Cl | H           | H    | —(CH$_2$)$_4$—       | 5 | 5 | 5 | 5 | 5 | 25  | 25  | N   | 25 |
| 28 | 5-Cl | —CH$_3$     | H    | —(CH$_2$)$_2$—       | 5 | 5 | 5 | 5 | 5 | 25  | 25  | N   | 25 |
| 29 | 5-Cl | H           | H    | —CH$_2$—CH(CH$_3$)— | 5 | 5 | 5 | 5 | 5 | 25  | 25  | 100 | 25 |
| 30 | 5-Cl | H           | H    | —CH(CH$_3$)—CH$_2$— | 5 | 5 | 5 | 5 | 5 | 25  | 25  | N   | 25 |
| 31 | 5-Cl | H           | H    | —CH$_2$—C(CH$_3$)$_2$— | 5 | 5 | 5 | 5 | 5 | 25  | 25  | N   | 25 |
| 32 | H    | —CH$_3$     | H    | —(CH$_2$)$_2$—       | 5 | 5 | 5 | 5 | 5 | 25  | 25  | 100 | 25 |
| 33 | H    | H           | H    | —CH$_2$C(CH$_3$)$_2$— | 5 | 5 | 5 | 5 | 5 | 25  | 25  | 100 | 25 |
| 34 | 5-F  | H           | H    | —(CH$_2$)$_2$—       | 5 | 5 | 5 | 5 | 5 | 25  | 25  | 100 | 25 |
| 35 | H    | —CH$_3$     | —CH$_3$ | —(CH$_2$)$_2$—    | 5 | 5 | 5 | 5 | 5 | 100 | 25  | N   | 25 |
| 36 | 5-F  | —CH$_3$     | H    | —(CH$_2$)$_2$—       | 5 | 5 | 5 | 5 | 5 | 25  | 25  | 25  | 25 |
| 37 | 5-F  | H           | H    | —(CH$_2$)$_2$—       | 5 | 5 | 5 | 5 | 5 | 25  | 25  | 100 | 25 |
| 38 | 5-F  | H           | H    | —CH$_2$—C(CH$_3$)$_2$— | 5 | 5 | 5 | 5 | 5 | 25  | 25  | 100 | 25 |
| 39 | 5-F  | H           | H    | —(CH$_2$)$_4$—       | 5 | 5 | 5 | 5 | 5 | 100 | 100 | N   | 25 |
| 40 | H    | —C(CH$_3$)  | H    | —(CH$_2$)$_2$—       | 5 | 5 | 5 | 5 | 5 | 25  | 25  | 25  | 25 |
| 41 | H    | —CH$_2$CH$_3$ | H  | —(CH$_2$)$_2$—       | 5 | 5 | 5 | 5 | 5 | 25  | 25  | 25  | 25 |
| 42 | H    | —(CH$_2$)$_2$CH$_3$ | H | —(CH$_2$)$_2$—   | 5 | 5 | 5 | 5 | 5 | 25  | 25  | 25  | 25 |

TABLE 8-continued

|  |  |  |  |  | Fungi | | | | | Bacteria | | | |
|---|---|---|---|---|---|---|---|---|---|---|---|---|---|
| Example | $R^7$ | $R^3$ | $R^4$ | Y | AN | CA | AP | GR | PP | EC | PA | SA | BS |
| 43 | H | —(CH$_2$)$_3$CH$_3$ | H | —(CH$_2$)$_2$— | 5 | 5 | 5 | 5 | 5 | 25 | 25 | 25 | 25 |
| 44 | H | —(CH$_2$)$_4$CH$_3$ | H | —(CH$_2$)$_2$— | 5 | 25 | 5 | 5 | 5 | N | 100 | 25 | 100 |
| 45 | H | H | H | —CH(CH$_3$)—CH$_2$— | 5 | 5 | 5 | 5 | 5 | 100 | N | 25 | 25 |
| 46 | 5-Cl | H | H | —CH—(CH$_2$CH$_3$)CH$_2$— | 5 | 5 | 5 | 5 | 5 | 100 | N | 25 | N |
| 47 | 5-Cl | H | H | —CH$_2$—CH(CH$_2$CH$_3$)— | 5 | 5 | 5 | 5 | 5 | 25 | N | 25 | N |
| 48 | H | H | H | —CH$_2$CH(CH$_3$)— | 5 | 5 | 5 | 5 | 5 | 25 | N | 25 | 100 |
| 49 | H | H | H | —CH$_2$CH(CH$_2$CH$_3$)— | 5 | 5 | 5 | 5 | 5 | 25 | N | 25 | 25 |
| 50 | H | H | H | —CH(CH$_2$CH$_3$)CH$_2$— | 5 | 5 | 5 | 5 | 5 | 100 | N | 25 | 100 |
| 51 | H | H | H | —CH$_2$CH((CH$_2$)$_3$CH$_3$)— | 5 | 5 | 5 | 5 | 5 | 100 | N | 25 | 100 |
| 52 | H | H | H | —CH$_2$CH(CH$_2$CH(CH$_3$)$_2$)— | 5 | 5 | 5 | 5 | 5 | 100 | N | 25 | 100 |
| 53 | H | H | H | —CH$_2$CH((CH$_2$)$_2$CH$_3$)— | 5 | 5 | 5 | 5 | 5 | 25 | 100 | 25 | 25 |
| 54 | H | H | H | —CH$_2$CH((CH$_2$)$_2$SCH$_3$)— | 5 | 5 | 5 | 5 | 5 | 25 | 100 | 100 | 25 |
| 55 | 5-F | —CH$_2$CH$_3$ | H | —(CH$_2$)$_2$— | 5 | 5 | 5 | 5 | 5 | 25 | N | 100 | 25 |
| 56 | 5-F | H | H | —CH$_2$CH(CH$_2$CH$_3$)— | 5 | 5 | 5 | 5 | 5 | 25 | N | 100 | 25 |
| 57 | 5-F | H | H | —CH(CH$_2$CH$_3$)CH$_2$— | 5 | 5 | 5 | 5 | 5 | 25 | N | 100 | 25 |
| 58 | 5-F | —(CH$_2$)$_2$CH$_3$ | H | —(CH$_2$)$_2$— | 5 | 5 | 5 | 5 | 5 | 25 | N | 100 | 25 |
| Control | H | — | — | — | 25 | 25 | 5 | 5 | 5 | 100 | N | N | 25 |

Footnote to Table 8
N = no activity at 100 ppm level
Control = boronophthalide
AN = *Aspergillus niger*
AP = *Aureobasidium pullulans*
CA = *Candida albicans*
GR = *Gliocladium roseum*
PP = *Penicillium pinophylum*
BS = *Bacillus subtilis*
EC = *Escherichia coli*
PA = *Pseudomonas aeruginosa*
SA = *Staphylococcus aureus*

Microbiological Examples 59 to 78

Examples 23 to 58 were repeated and the MIC value for benzoxaboroles of the following structure determined.

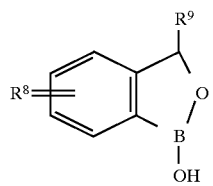

$R^8$ represents one or more substituents in the phenyl ring.
The results are given in Table 9 below.

TABLE 9

|  |  |  | Fungi | | | | | Bacteria | | | |
|---|---|---|---|---|---|---|---|---|---|---|---|
| Example | $R^8$ | $R^9$ | AN | CA | AP | GR | PP | EC | PA | SA | BS |
| 59 | 6-Cl | H | 100 | 100 | 100 | 5 | 5 | N | N | N | N |
| 60 | 5-PhO | H | 5 | 5 | 5 | 5 | 5 | 25 | N | 25 | 25 |
| 61 | 5-C(CH$_3$)$_3$ | H | 100 | 100 | 100 | 100 | 100 | 100 | N | 100 | 100 |
| 62 | 4,5 fused Ph | H | 25 | 25 | 25 | 25 | 25 | 100 | N | 25 | 25 |
| 63 | 5,6 fused Ph | H | 25 | 25 | 25 | 25 | 25 | N | 100 | 100 | 100 |
| 64 | 5-F | H | 5 | 5 | 5 | 5 | 5 | 100 | N | N | 25 |
| 65 | H | Ph | N | N | 100 | 100 | 100 | N | N | N | N |
| 66 | 5-Cl | H | 5 | 5 | 5 | 5 | 5 | N | N | N | N |
| 67 | 5-CF$_3$ | H | 25 | 25 | 25 | 25 | 25 | N | N | N | 25 |
| 68 | 5-Br | H | 5 | 25 | 5 | 5 | 5 | 100 | 100 | 25 | 25 |
| 69 | 4-F | H | 100 | 100 | 25 | 25 | 100 | 100 | N | 100 | 25 |
| 70 | 6-F | H | 100 | 25 | 25 | 25 | 25 | 25 | N | 100 | 25 |
| 71 | H | —CN | N | N | N | N | N | N | N | N | N |
| 72 | 4-CH$_3$, 5-F | H | N | N | N | N | N | N | N | N | N |
| 73 | 5,6 diF | H | 25 | 25 | 25 | 5 | 5 | 25 | N | N | 25 |
| 74 | 5-CH$_3$O | H | 250 | 125 | 62.5 | 125 | 250 | 250 | 250 | 250 | 500 |

TABLE 9-continued

| | | | Fungi | | | | | Bacteria | | | |
|---|---|---|---|---|---|---|---|---|---|---|---|
| Example | R⁸ | R⁹ | AN | CA | AP | GR | PP | EC | PA | SA | BS |
| 74 | 7-F | H | 16 | 16 | 16 | 31 | 16 | 125 | 250 | 125 | 8 |
| 76 | 4,7 diF | H | | | | | | | | | |
| 77 | 6,7 diF | H | | | | | | | | | |
| 78 | 5,7 diF | H | | | | | | | | | |
| Control | H | H | 25 | 25 | 5 | 5 | 5 | ioO | N | N | 25 |

Footnote to Table 9
Control is boronophthalide (R⁸ = R⁹ = H)

Examples 79 and 80

Examples 23 to 58 were repeated and the MIC values for benzoxaboroles of the following structure determined

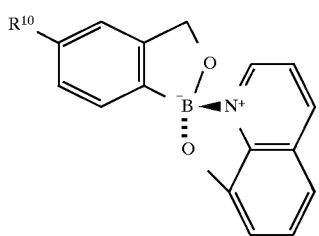

The results are given in Table 10 below.

TABLE 10

| | | Fungi | | | | | Bacteria | | | |
|---|---|---|---|---|---|---|---|---|---|---|
| Example | R¹⁰ | AN | CA | AP | GR | PP | EC | PA | SA | BS |
| 79 | H | 25 | 25 | 25 | 25 | 25 | 100 | 100 | 25 | 25 |
| 80 | F | 5 | 5 | 5 | 5 | 5 | 25 | 25 | 25 | 25 |

Plastics Deteriogen Examples 23–34, 36–58, 68 and 80

Determination of Activity against plastics deteriogens

Examples 15 to 18 were repeated using certain of the examples listed in Examples 23 to 78. The activity of the various benzoxaboroles is listed in Table 11 below. The example reference numbers listed in Table 8 and 9 are retained.

TABLE 11

| Example | AP | FS | PF | SB | SW |
|---|---|---|---|---|---|
| 23 | 1.25 | 1.25 | 1.25 | 1.25 | 2.5 |
| 24 | 1.25 | 1.25 | 2.5 | 2.5 | 5.0 |
| 25 | 1.25 | 2.5 | 2.5 | 2.5 | 20 |
| 26 | 1.25 | 1.25 | 1.25 | 1.25 | 2.5 |
| 27 | 1.25 | 1.25 | 1.25 | 1.25 | 2.5 |
| 28 | 1.25 | 1.25 | 1.25 | 1.25 | 1.25 |
| 29 | 1.25 | 1.25 | 1.25 | 1.25 | 1.25 |
| 30 | 1.25 | 1.25 | 1.25 | 1.25 | 1.25 |
| 31 | 1.25 | 1.25 | 1.25 | 1.25 | 1.25 |
| 32 | 1.25 | 1.25 | 1.25 | 1.25 | 1.25 |
| 33 | 1.25 | 1.25 | 1.25 | 1.25 | 1.25 |
| 34 | 1.25 | 1.25 | 1.25 | 1.25 | 1.25 |
| 36 | 1.25 | 1.25 | 1.25 | 1.25 | 5.0 |
| 37 | 1.25 | 1.25 | 1.25 | 1.25 | 5.0 |

TABLE 11-continued

| Example | AP | FS | PF | SB | SW |
|---|---|---|---|---|---|
| 38 | 1.25 | 1.25 | 1.25 | 1.25 | 5.0 |
| 39 | 1.25 | 1.25 | 1.25 | 1.25 | 5.0 |
| 40 | 2.5 | 1.25 | 1.25 | 1.25 | 1.25 |
| 41 | 1.25 | 1.25 | 1.25 | 1.25 | 1.25 |
| 42 | 2.5 | 2.5 | 1.25 | 1.25 | 1.25 |
| 43 | 2.5 | 2.5 | 1.25 | 1.25 | 1.25 |
| 44 | 1.25 | 1.25 | 1.25 | 1.25 | 1.25 |
| 45 | 1.25 | 1.25 | 1.25 | 1.25 | 1.25 |
| 46 | 1.25 | 1.25 | 1.25 | 1.25 | 1.25 |
| 47 | 1.25 | 1.25 | 1.25 | 1.25 | 1.25 |
| 48 | 1.25 | 1.25 | 1.25 | 1.25 | 1.25 |
| 49 | 1.25 | 1.25 | 1.25 | 1.25 | 1.25 |
| 50 | 1.25 | 1.25 | 1.25 | 1.25 | 1.25 |
| 51 | 1.25 | 1.25 | 1.25 | 1.25 | 1.25 |
| 52 | 1.25 | 1.25 | 1.25 | 1.25 | 1.25 |
| 53 | 1.25 | 1.25 | 1.25 | 1.25 | 1.25 |
| 54 | 5.0 | 1.25 | 5.0 | 1.25 | 5.0 |
| 55 | 2.5 | 1.25 | 1.25 | 1.25 | 1.25 |
| 56 | 1.25 | 1.25 | 1.25 | 1.25 | 1.25 |
| 57 | 1.25 | 1.25 | 1.25 | 1.25 | 1.25 |
| 58 | 1.25 | 1.25 | 1.25 | 1.25 | 1.25 |
| 68 | 5.0 | 5.0 | 1.25 | 1.25 | 1.25 |
| 80 | 1.25 | 1.25 | 1.25 | 1.25 | 1.25 |
| Control 1 | 2.5 | 2.5 | 2.5 | 2.5 | 20.0 |
| Control 2 | 2.5 | 20 | 2.5 | 1.25 | 1.25 |

Footnote to Table 11
Control 1 is boronophthalide
Control 2 is 2-n-octylisothiazolin-3-one

We claim:

1. A method for the protection of a medium susceptible to microbial attack by the treatment of the medium with an effective amount of an oxaborole of formula (1)

or a salt thereof:
wherein
A and D together with the carbon atoms to which they are attached form a 5, 6, or 7-membered fused ring which may be substituted by $C_{1-6}$-alkyl, $C_{1-6}$-alkoxy, hydroxy, halogen, nitro, nitrile, amino, amino substituted by one or more $C_{1-6}$-alkyl groups, , carboxy, acyl, aryloxy, carbonamido, carbonamido substituted by $C_{1-6}$-alkyl, sulphonamido or trifluoromethyl or the fused ring may link two oxaborole rings;
X is a group —$CR^1R^2$ wherein $R^1$ and $R^2$ are each, independently, hydrogen, $C_{1-6}$-alkyl, nitrile, nitro, aryl, aralkyl or $R^1$ and $R^2$ together with the carbon atom to which they are attached form an alicyclic ring; and R is hydrogen, $C_{1-18}$-alkyl, ($C_{1-18}$-alkyl substituted by $C_{1-6}$-alkoxy, $C_{1-6}$-alkylthio, hydroxy, amino, amino substituted by $C_{1-18}$-alkyl, , carboxy, aryl, aryloxy, carbonamido, ( carbonamido substituted by $C_{1-6}$-alkyl, aryl or aralkyl), aralkyl, aryl, heteroaryl, cycloalkyl, $C_{1-18}$-alkyleneamino, $C_{1-18}$-alkyleneamino substituted by phenyl, $C_{1-6}$-alkoxy or $C_{1-6}$-alkylthio, carbonyl alkyleneamino or a radical of formula (2)

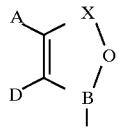
(2)

wherein A, D and X are as defined hereinbefore except for boronophthalide.

2. A method as claimed in claim 1 wherein A and D together with the carbon atoms to which they are attached form a fused phenyl ring.

3. A method as claimed in either claim 1 or claim 2 wherein the fused ring is substituted by halogen.

4. A method as claimed in claim 3 wherein R is hydrogen.

5. A method as claimed in claim 1 wherein the heteroaryl substituent represented by R is quinolinyl.

6. A method as claimed in claim 1 wherein the oxaborole is a compound of formula 3

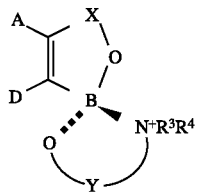
(3)

wherein
A, D and X are as defined in claim 1;
Y is a divalent alkylene linking group containing up to 18 carbon atoms or a divalent alkylene linking group containing up to 18 carbon atoms which is substituted by phenyl, $C_{1-6}$alkoxy, $C_{1-6}$-alkylthio; carbonyl alkylene amino; and
$R^3$ and $R^4$ are each, independently, hydrogen, $C_{1-18}$-alkyl or phenyl or $R^3$ together with Y or part of Y forms a 5-, 6- or 7-membered ring containing the nitrogen atom.

7. A method as claimed in claim 5 wherein the oxaborole is a compound of formula 4

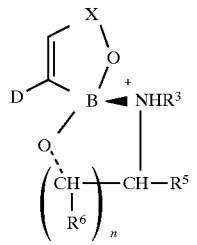
(4)

wherein
A, D and X are as defined in claim 1;
n is 1, 2 or 3;
$R^3$ is hydrogen, $C_{1-18}$-alkyl or phenyl; and
$R^5$ and $R^6$ are each, independently, hydrogen, alkyl containing up to a total of 16 carbon atoms or phenyl.

8. A method as claimed in claim 7 wherein the medium is a paint film or a plastics material.

9. A compound of formula (1)

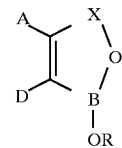
(1)

or a salt thereof
wherein A, D, R and X are as defined in claim 1 except for 1,1'-oxybis;
1,1'-oxybis; 3,7-dihydro-1,5-dihydroxy-1H, 3H-benzo bis oxaborole; boronophthalide and boronophthalide containing the following substituent(s):-6-nitro-, 6-amino-, 7-methyl-, 6-(NN-dimethylamino)-, 5-(NN-dimethylamino)-, 4-bromo-, 6-methyl, 1-benzyloxy-, 1-cyclohexyloxy-, 1-ethoxy-, 3-methyl and 3-cyano.

10. A compound as claimed in claim 9 which is of formula 3

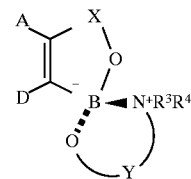
(3)

wherein
A, D and X are as defined in claim 1;
$R^3$ and $R^4$ are each, independently, hydrogen, $C_{1-18}$-alkyl or phenyl or the group —$NR^3R^4$ together with Y or part of Y forms a 5-, 6- or 7-membered ring containing the nitrogen atom; and
Y is as defined in claim 6.

11. A compound as claimed in either claim 9 or claim 10 wherein the fused ring formed by A and D together with the carbon atoms to which they are attached is a phenyl ring.

12. A compound as claimed in claim 11 which is an ester derived from 5- or 6-chloro, 5- or 6-bromo or 5- or 6-fluoro benzoxaborole.

13. A composition comprising a carrier and an oxaborole of formula 1

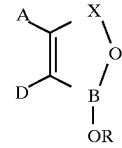
(1)

or a salt thereof:
wherein A, D, X and R are as defined in claim 1 except where the oxaborole is boronophthalide.

14. A composition as claimed in claim 13 wherein the carrier is a paint film or a plastics material.

15. A composition as claimed in claim 14 wherein the plastics material is placticised PVC or polyurethane.

16. A composition as claimed in claim 13 wherein the carrier is a stabiliser or plasticiser for a plastics material.

17. A composition as claimed in claim 16 wherein the stabiliser or plasticiser is dioctylphthalate, dioctyl adipate or expoxidised soya bean oil.

18. A process for making an oxaborole of formula 1 wherein A and D together with the carbon atoms to which they are attached form a fused phenyl ring which comprises reacting on o-substituted halogeno toluene with magnesium or alkyl-lithium in a inert solvent and reacting the Grignard reagent or aryl lithium so formed with a borate ester to obtain a toluene boronic acid which is then reacted with a brominating agent followed by hydrolysis to give a hydroxymethylbenzene boronic acid and cyclising the boronic acid under acid conditions to give a benzoxaborole.

19. A process for making an oxaborole of formula 1 wherein A and D together with the carbon atoms to which they are attached form a fused phenyl ring which comprises reacting an optionally substituted benzaldehyde with p-toluenesulphonylhydrazide in an inert solvent followed by reaction with boron tribromide and catalyst to give a 1,2-dihydro-1-hydroxy-2-(4-methylphenylsulphonyl)-2,3,1-benzodiazaborine which is then hydrolysed and cyclised to form a benzoxaborole.

20. A process for making an oxaborole ester as claimed in claim 10 which comprises reacting an oxaborole of formula 1 where R is hydrogen with an amino-aliphatic carboxylic acid, alkanolamine or 8-hydroxyquinoline in an inert solvent at 25°–125° C.

21. A process for making an oxaborole of formula 1 wherein A and D together with the carbon atoms to which they are attached form a fused aromatic ring which comprises reacting an aromatic compound containing a —CH$_2$OH group with alkyl or aryl-lithium and an organoborate in a dry inert liquid.

22. A process as claimed in claim 21 wherein the aromatic compound containing a CH$_2$OH group also contains one or more further substituents which are ortho-lithiation activating groups.

23. A process for making an oxaborole of formula 1 wherein A and D together with the carbon atoms to which they are attached form a fused aromatic ring which comprises reacting an aromatic compound containing a —CH$_2$OH group and an ortho chloro or fluoro group with alkyl or aryl lithium and an organo-borate in an inert organic liquid.

* * * * *